United States Patent
Yamada et al.

(10) Patent No.: US 7,221,689 B2
(45) Date of Patent: May 22, 2007

(54) LASER APPARATUS

(75) Inventors: Tsuyoshi Yamada, Toyota (JP); Yasutoshi Takada, Kawasaki (JP)

(73) Assignee: Nidek Co., Ltd., Gamagori-shi (JP)

( * ) Notice: Subject to any disclaimer, the term of this patent is extended or adjusted under 35 U.S.C. 154(b) by 295 days.

(21) Appl. No.: 10/796,018

(22) Filed: Mar. 10, 2004

(65) Prior Publication Data

US 2004/0240494 A1 Dec. 2, 2004

(30) Foreign Application Priority Data

Mar. 14, 2003 (JP) ............................. 2003-069191

(51) Int. Cl.
*H01S 3/10* (2006.01)
*H01S 3/082* (2006.01)

(52) U.S. Cl. .............................. 372/22; 372/23; 372/97

(58) Field of Classification Search .................. 372/21, 372/22, 23, 97
See application file for complete search history.

(56) References Cited

U.S. PATENT DOCUMENTS

| | | | |
|---|---|---|---|
| 4,425,648 A | | 1/1984 | Holly |
| 4,637,026 A | * | 1/1987 | Liu ............... 372/22 |
| 5,144,630 A | | 9/1992 | Lin |
| 5,249,192 A | * | 9/1993 | Kuizenga et al. .............. 372/23 |
| 5,268,775 A | * | 12/1993 | Zeidler ............................. 349/5 |
| 5,289,479 A | * | 2/1994 | Oka et al. ....................... 372/22 |
| 5,331,649 A | | 7/1994 | Dacquay et al. |
| 5,345,457 A | | 9/1994 | Zenzie et al. |
| 5,528,612 A | | 6/1996 | Scheps et al. |
| 5,734,504 A | * | 3/1998 | Billman ....................... 359/618 |
| 5,774,269 A | * | 6/1998 | Snoeren ....................... 359/636 |
| 6,596,984 B2 | * | 7/2003 | Vrehen ....................... 250/234 |
| 6,636,537 B2 | | 10/2003 | Takada |
| 2002/0027932 A1 | * | 3/2002 | Takada ....................... 372/23 |
| 2002/0061037 A1 | | 5/2002 | Schmid et al. |
| 2004/0095637 A1 | * | 5/2004 | Nikolov et al. ............. 359/352 |

FOREIGN PATENT DOCUMENTS

| | | |
|---|---|---|
| JP | 10-65238 | 3/1998 |
| JP | 2001-257398 | 9/2001 |
| JP | 2002-134816 | 5/2002 |

(Continued)

OTHER PUBLICATIONS

P.D. Hale et al., Stability of Birefringenet Linear Retarders (Waveplates), Applied Optics, vol. 27, No. 24, Dec. 15, 1988, pp. 5146-5153.*

(Continued)

*Primary Examiner*—James Menefee
(74) *Attorney, Agent, or Firm*—Oliff and Berridge, PLC

(57) ABSTRACT

A laser apparatus capable of emitting laser beams of a plurality of different wavelengths includes: a solid-state laser medium which emits light of a plurality of different peak wavelengths; a resonance optical system which resonates the emitted light of the plurality of different peak wavelengths and converts respective light to oscillate the laser beams of the plurality of different wavelengths; and a ¼ wave plate for a wide band, which is placed in the resonance optical system and has a property of providing a uniform phase difference to the light of the plurality of different peak wavelengths to be converted.

2 Claims, 5 Drawing Sheets

FOREIGN PATENT DOCUMENTS

JP          2002-151774          5/2002
JP          2003-204099          7/2003

OTHER PUBLICATIONS

Michio Oka et al., Stable Intracavity Doubling of Orthogonal Linearly Polarized Modes in Diode-Pumped Nd:YAG Lasers, Optics Letters, vol. 13, No. 10, Oct. 1988, pp. 805-807.*

Clarkson et al.; "Simple method for reducing the depolarization loss resulting from thermally induced birefringence in solid-state lasers"; Optics Letters, vol. 24, No. 12; Jun. 15, 1999; pp. 820-822.

Extended Abstracts (The 63rd Autumn Meeting, 2002); The Japan Society of Applied Physics; Sep. 24-Sep. 27, 2002.

Extended Abstracts (The 50th Spring Meeting, 2003); The Japan Society of Applied and Related Societies; Mar. 27-Mar. 30, 2003.

Extended Abstracts (The 64th Autumn Meeting, 2003); The Japan Society of Applied Physics; Aug. 30-Sep. 2, 2003.

Reports on the 313th Topical Meeting of the Laser Society of Japan; Sep. 17, 2003.

Program (24th Annual Meeting of Japan Society for Laser Surgery and Medicine); Nov. 14-Nov. 15, 2003.

Digest of Technical Papers; (24th Annual Meeting of the Laser Society of Japan); Jan. 29-Jan. 30, 2004.

* cited by examiner

FIG. 4

| Wavelength (nm) | Case without 1/4 wave plate | | Case with 1/4 wave plate | |
|---|---|---|---|---|
| | Output Power (W) | Power Variation (%) | Output Power (W) | Power Variation (%) |
| 532 (green) | 4.5 | ±9 | 5.0 | ±4 |
| 561 (yellow) | 1.1 | ±15 | 1.5 | ±8 |
| 659 (red) | 0.8 | ±20 | 1.5 | ±8 |

LASER APPARATUS

BACKGROUND OF THE INVENTION

1. Field of the Invention

The present invention relates to a laser apparatus capable of emitting laser beams of a plurality of different wavelengths.

2. Description of Related Art

As a laser apparatus capable of emitting laser beams of a plurality of different wavelengths, there have been known an apparatus using a solid-state laser and a wavelength converting element (a wavelength selecting element), in addition to an apparatus using an argon dye laser, a krypton laser, or the like. In the laser apparatus using the solid-state laser, the effect of thermal birefringence (or thermally induced birefringence) may be caused by heat generation of a laser crystal (a laser medium) itself, leading to a loss in a resonator, with the result that laser output power is reduced.

SUMMARY OF THE INVENTION

The present invention has been made in view of the above circumstances and has an object to overcome the above problems and to provide a laser apparatus capable of efficiently and stably emitting laser beams different in wavelength.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser apparatus capable of emitting laser beams of a plurality of different wavelengths, the apparatus including: a solid-state laser medium which emits light of a plurality of different peak wavelengths; a resonance optical system which resonates the emitted light of the plurality of different peak wavelengths and converts respective light to oscillate the laser beams of the plurality of different wavelengths; and a ¼ wave plate for a wide band, which is placed in the resonance optical system and has a property of providing a uniform phase difference to the light of the plurality of different peak wavelengths to be converted.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIG. 4 is a table showing laser output power and power variation (stability) in a case with a wave plate and another case without a wave plate.

DETAILED DESCRIPTION OF THE PREFERRED EMBODIMENTS

Figure 1:
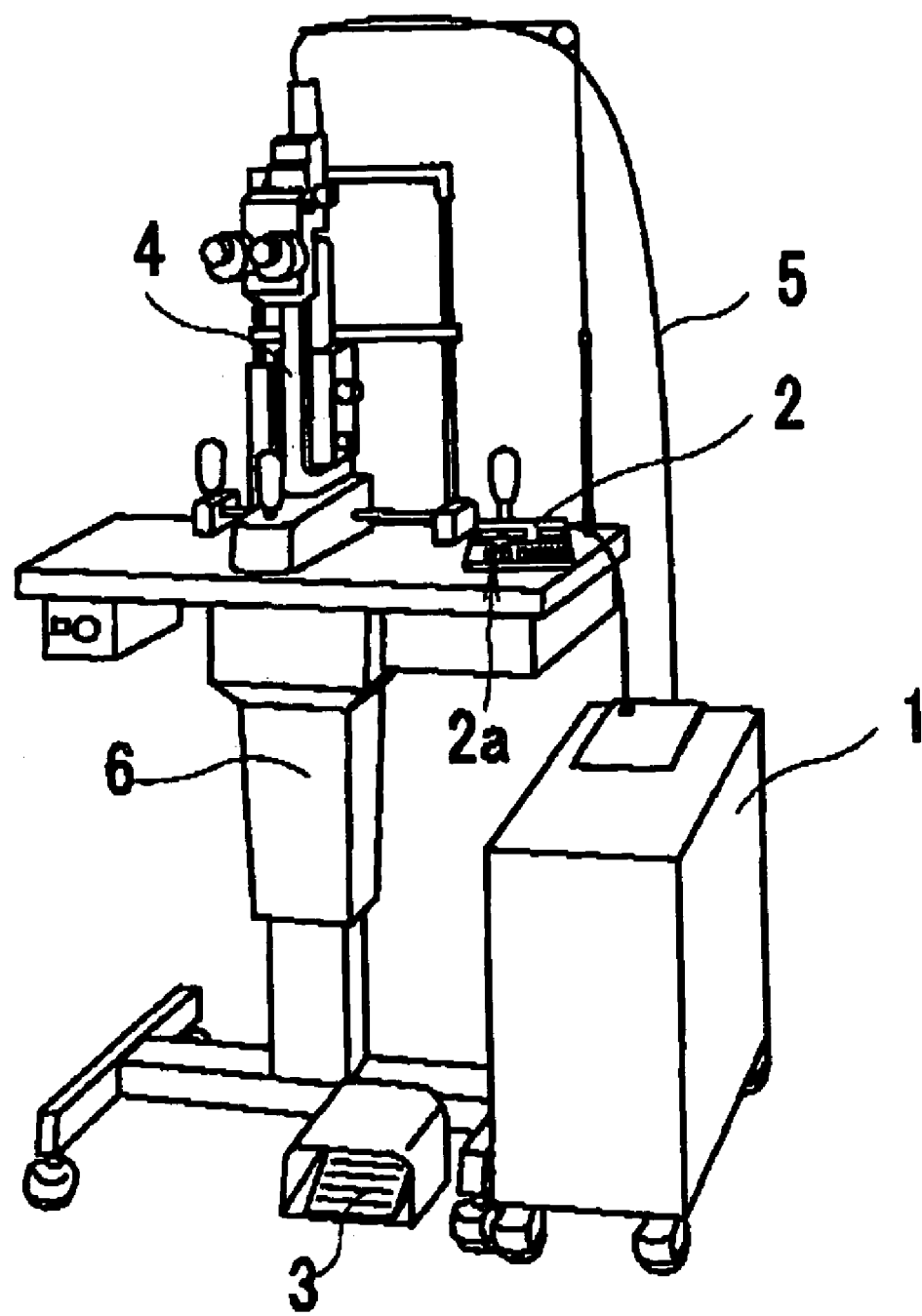
FIG. 1 is a schematic perspective view of a laser apparatus in an embodiment.
Figure 2:
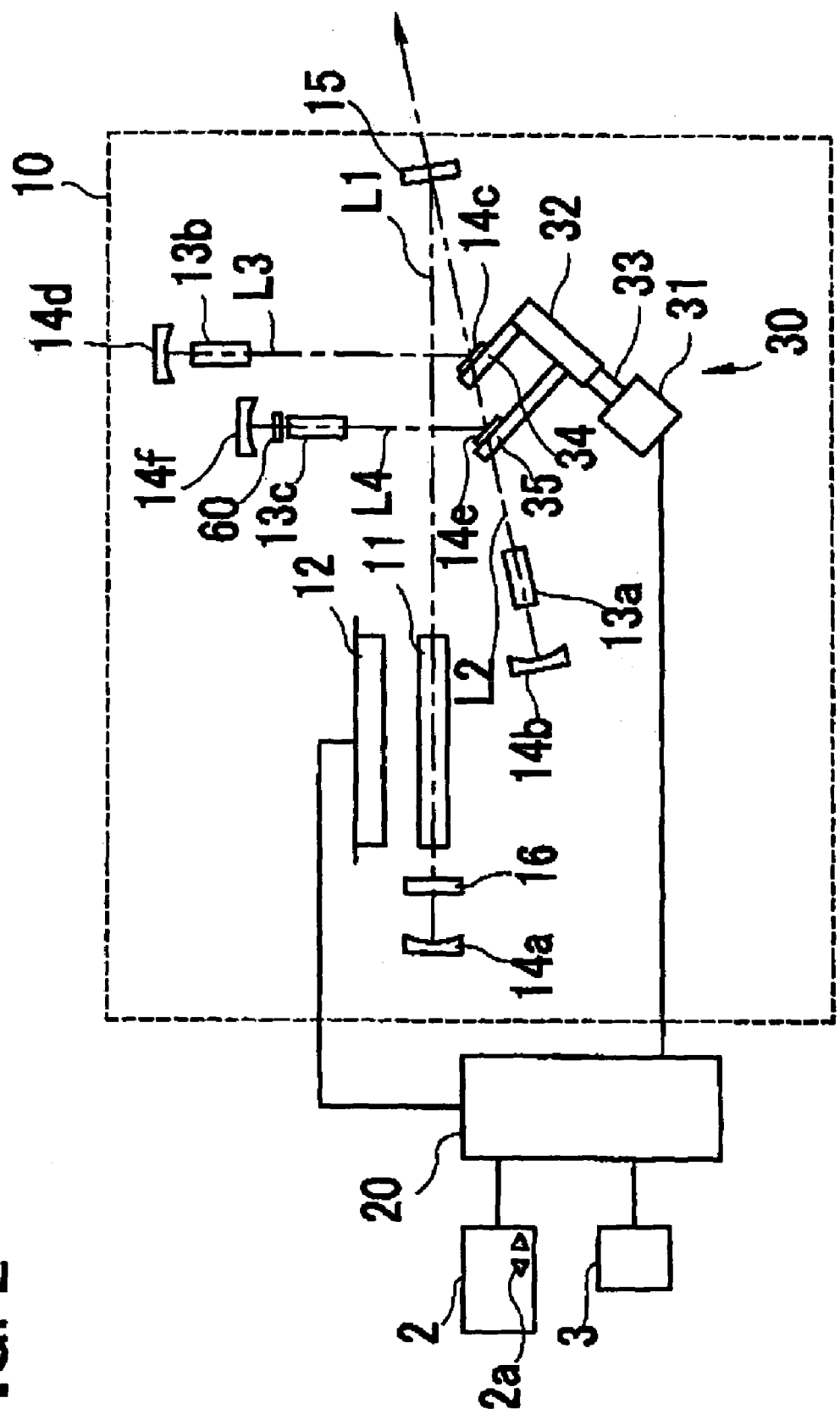
FIG. 2 is a schematic diagram of an optical system and a control system in the laser apparatus.

A detailed description of a preferred embodiment of a laser apparatus embodying the present invention will now be given referring to the accompanying drawings. The following explanations are made on a laser apparatus which selectively emits laser beams of three wavelengths. FIG. 1 is a perspective view of an ophthalmic photocoagulation laser apparatus using a slit lamp. FIG. 2 is a schematic diagram of an optical system and a control system in the apparatus.

A main body 1 of the laser apparatus houses a laser oscillator (a resonator) 10, a part of a light delivery optical system for delivering a laser beam to an affected part of a patient's eye to irradiate the affected part, a control section 20, and others. A control box 2 is provided thereon with a wavelength selection switch 2a to be used for selecting a wavelength of a laser beam and other various switches for setting laser irradiation conditions. A footswitch 3 is used for generating a trigger signal to start laser irradiation.

A slit lamp 4 contains an observation optical system for allowing an operator to observe the patient's eye and a part of the light delivery optical system. An optical fiber 5 is used to deliver the laser beam from the main body 1 to the slit lamp 4. A stand 6 mounts thereon the slit lamp 4 and is moved in a vertical direction.

The laser oscillator 10 is internally provided with an Nd:YAG crystal 11 (hereinafter, referred to as "rod") which is a solid-state laser medium serving as a laser oscillating source, a laser diode 12 (hereinafter, referred to as "LD") serving as an exciting light source, nonlinear crystals 13a, 13b, and 13c (hereinafter, referred to as "NLC") serving as wavelength converters (wavelength converting elements), a ¼ wave plate 16 for a wide band, total reflection mirrors (high reflectors) 14a to 14f (hereinafter, referred to as "HR"), and an output mirror 15.

The Nd:YAG crystal emits light having a plurality of oscillation lines (peak wavelengths) in the infrared region by an exciting light from the exciting light source. Therefore, the apparatus in the present embodiment is constructed such that each second harmonic light of three oscillation lines; about 1064 nm, about 1123 nm, about 1319 nm (hereinafter, "about" is omitted), which are the wavelengths with high power among the plural oscillation lines emitted from the above crystal, is generated with the use of the nonlinear crystal, thereby emitting (oscillating) laser beams of three different wavelengths (three different colors) of about 532 nm (green), about 561 nm (yellow), and about 659 nm (red) (hereinafter, "about" is omitted), respectively. It is to be noted that the nonlinear crystals may be selected from among KTP crystal, LBO crystal, BBO crystal, or the like. In the present embodiment, the KTP crystal is used for 532 nm and the LBO crystal is used for 561 nm and 659 nm, respectively.

On the optical path of an optical axis L1 on which the rod 11 is placed, an HR 14a is disposed at one end thereof, and the output mirror 15 is arranged at a predetermined inclination angle at the other end. The HR 14a in the present embodiment has the property of totally reflecting the light of wavelengths of 1064 nm, 1123 nm, and 1319 nm. Instead of the HR 14a, another reflector capable of widely reflecting the light of wavelengths in the infrared region including 1064 nm, 1123 nm, and 1319 nm may be used. The output mirror 15 has the property of totally reflecting the light of wavelengths of 1064 nm, 1123 nm, and 1319 nm, while transmitting the light of wavelengths of 532 nm, 561 nm, and 659 nm.

On the optical path of an optical axis L2 in a reflecting direction of the output mirror 15, an NLC 13a and an HR 14b are placed. The NLC 13a generates the light of 659 nm which is the second harmonic light from the light of 1319 nm. The HR 14b has the property of totally reflecting the light of 1319 nm and the light of 659 nm.

The above optical arrangement constitutes a first resonance optical system including a resonator configuration constructed of a pair of the HR 14a on the optical axis L1 and the HR 14b on the optical axis L2, arranged as the rod 11 is located between them. Thus, the light of 659 nm generated by the NLC 13a can be emitted through the output mirror 15 without being blocked by the rod 11. It is preferable that the angle (the reflection angle) formed by the optical axis L1 and the optical axis L2 is as small as possible in light of the influence of aberration.

HR 14c and HR 14e, which are plane mirrors, are arranged to be movable onto/off from the optical path of the optical axis L2 between the output mirror 15 and the NLC 13a. The HR 14c has the property of totally reflecting the light of 1064 nm and the light of 532 nm. The HR 14e has the property of totally reflecting the light of 1123 nm and the light of 561 nm.

On the optical path of the optical axis L3 in a reflecting direction of the HR 14c, an NLC 13b and an HR 14d are placed. The NLC 13b generates the light of 532 nm which is the second harmonic light from the light of 1064 nm. The HR 14d has, as with the HR 14c, the property of totally reflecting the light of 1064 nm and the light of 532 nm.

On the optical path of the optical axis L4 in a reflecting direction of the HR 14e, an NLC 13c, a wavelength selecting element 60, and an HR 14f are placed. The NLC 13c generates the light of 561 nm which is the second harmonic light from the light of 1123 nm. As with the HR 14e, the HR 14f has the property of totally reflecting the light of 1123 nm and the light of 561 nm.

In the above optical arrangement, when the HR 14c is moved onto the optical path of the optical axis L2, the HR 14a, the rod 11, and the output mirror 15 of the first resonance optical system are also used to construct a second resonance optical system including a resonator constructed of a pair of the HR 14a and the HR 14d arranged as the rod 11 is located between them. When the HR 14e is moved onto the optical path of the optical axis L2, on the other hand, the HR 14a, the rod 11, and the output mirror 15 of the first resonance optical system are also used to construct a third resonance optical system including a resonator constructed of a pair of the HR 14a and the HR 14f arranged as the rod 11 is placed between them.

Figure 3:
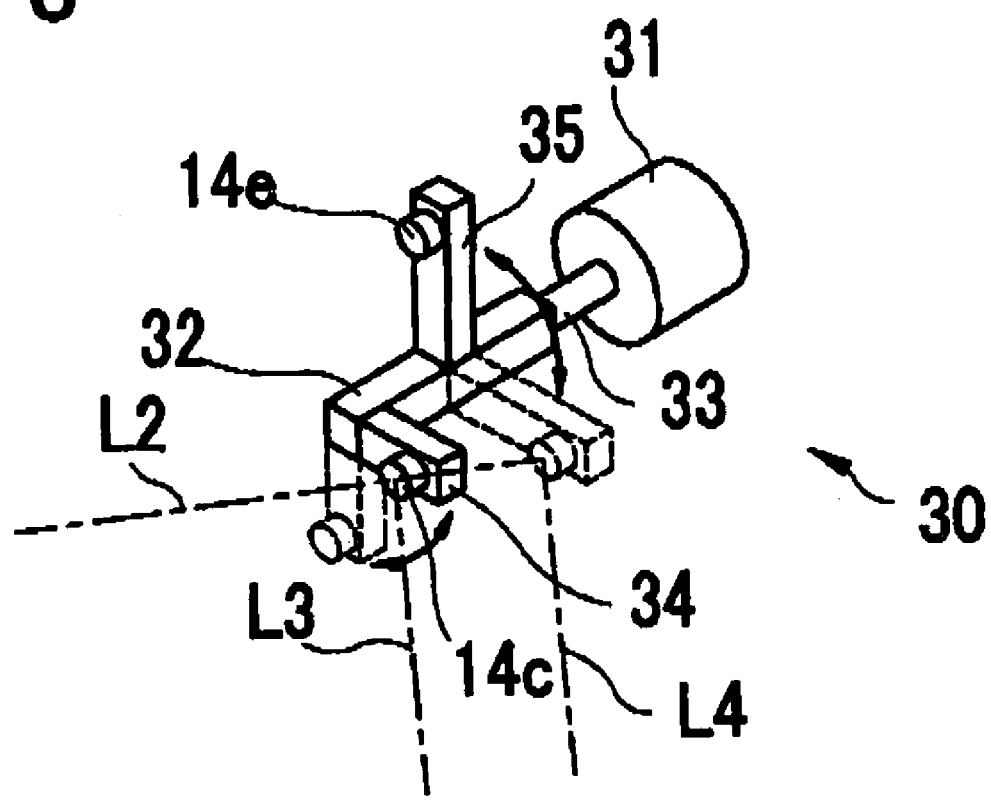
FIG. 3 is a schematic structural view of a device for inserting/removing a mirror.

The movement (insertion/removal) of the HR 14c and HR 14e with respect to the optical path of the optical axis L2 is conducted by an insertion/removal device 30. FIG. 3 a schematic structural view of the insertion/removal device 30.

A driving unit 31 in the present embodiment is a step motor. Instead of the step motor, furthermore, any unit of which a rotation angle is controllable can be used. The driving unit 31 is connected with a shaft 32 through a joint 33. Thus, the rotation of the driving unit 31 causes the shaft 32 to rotate. Two mirror holders 34 and 35 are mounted to the shaft 32 respectively at different axial angles to the rotation axis of the shaft 32. The HR 14c and HR 14e are attached to the mirror holders 34 and 35 respectively so that each reflection plane of the HRs 14c and 14e is perpendicular to the rotation axis of the shaft 32. With this structure, the HRs 14c and 14e are moved onto/off from the optical path of the optical axis L2 by the rotation of the driving unit 31, without changing the angle of each reflection plane to the optical axis L2.

When the HR 14c is set in a position shown by a solid line in FIG. 3, that is, when the HR 14c is placed on the optical path of the optical axis L2, the second resonance optical system is formed. On the other hand, when the HR 14e is set in a position shown by a dashed line in FIG. 3, that is, the HR 14e is placed on the optical path of the optical axis L2, the third resonance optical system is formed.

For reducing the thermal birefringence effect, the wave plate 16 is placed on a resonance optical path between the rod 11 and the HR 14a both arranged on the optical axis L1. This wave plate 16 is used to polarize the light of wavelengths in a wide region including a plurality of oscillation lines (peak wavelengths: 1064 nm, 1123 nm, 1319 nm) that are emitted from the rod 11.

Now, the need to reduce the thermal birefringence effect is described below. It is known that if any element for restricting polarization is not provided on the resonance optical path, bring a fundamental wave into a random polarized light, a polarization ratio (P/S) varies due to the thermal birefringence effect when the laser beam is emitted from the rod 11. The variation in the polarization ratio has a direct influence on a wavelength converting efficiency of the NLCs 13a, 13b, and 13c, which would become a major factor that causes unstable output of the second harmonic light. To remove such factor causing the unstable output of the second harmonic light, the wave plate 16 is placed on the resonance optical path.

Figure 5:
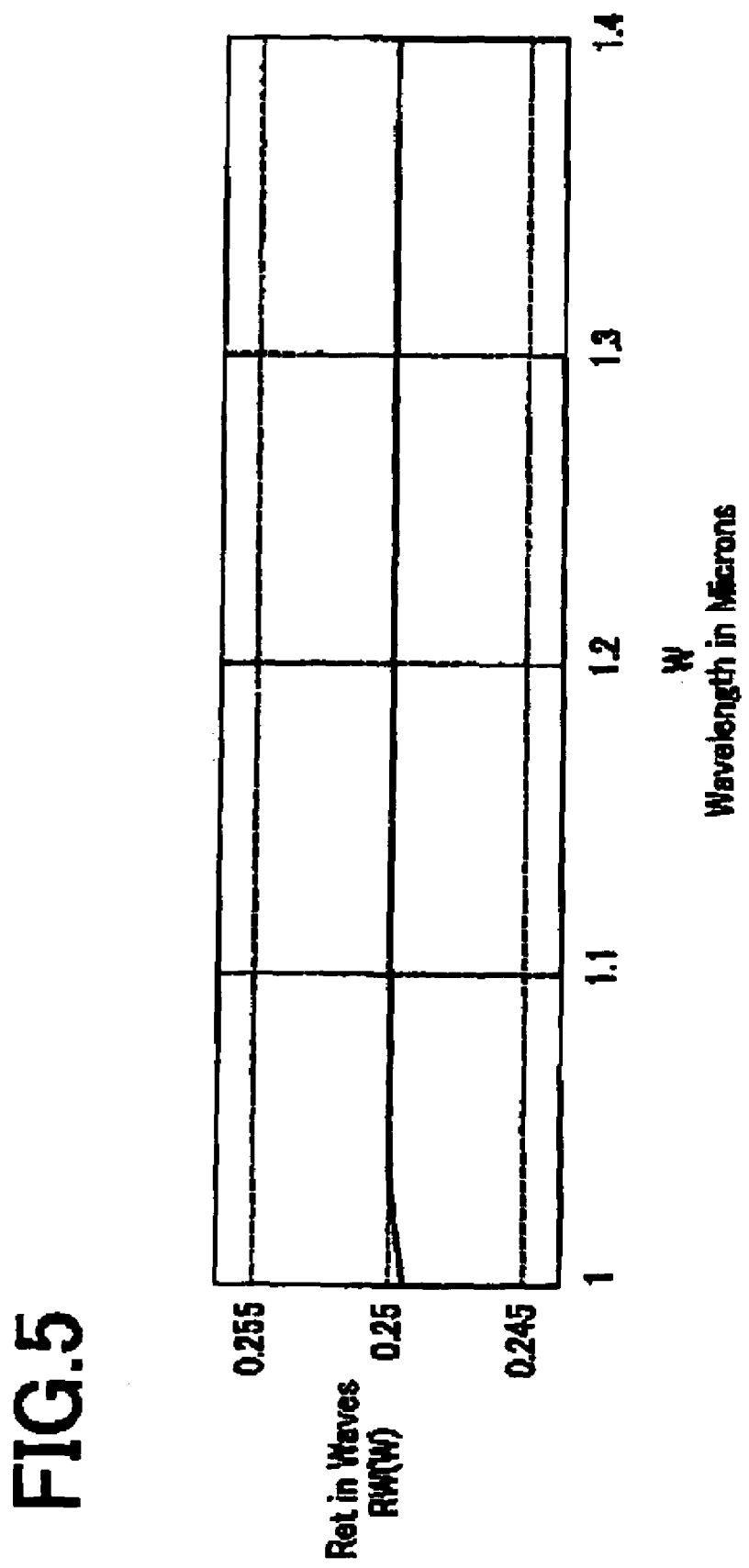
FIG. 5 is a graph showing the characteristics of the wave plate.

The wave plate 16 is constructed of a combination of a quartz plate and a magnesium fluoride plate and has the property of providing a flat phase difference to light of wavelengths in a wide region. The wave plate 16 used in the present embodiment has the property of providing a uniform phase difference (including an allowable range) to light of three wavelengths (1064 nm, 1123 nm, 1319 nm) to be converted. FIG. 5 is a graph showing the characteristics of the wave plate 16, in which a lateral axis indicates wavelengths in microns and a vertical axis indicates retardation (phase difference) in waves. As seen in FIG. 5, the wave plate 16 provides a uniform retardation of 0.25 to the light of three wavelengths (1064 nm, 1123 nm, 1319 nm). Optical contact is used for joining between the quartz plate and the magnesium fluoride plate in order to improve durability. The wave plate 16, on both sides (through which the optical axis L1 passes), is applied with an AR (anti reflective) coating to enhance transmittance to the light of three wavelengths (1064 nm, 1123 nm, 1319 nm).

The wave plate 16 has only to be placed on the resonance optical path between the rod 11 and the HR 14a. In light of durability, it is preferably placed in a position near the rod 11 where a beam diameter is maximum, that is, a power density is minimum.

The selection of the resonance optical systems is not limited to the selecting method in the present embodiment and alternatively may be performed by a method disclosed in U.S. Pat. No. 6,636,537 (corresponding to Japanese patent unexamined publication No. 2002-151774) and other well known methods.

The laser apparatus having the above described structure will be explained in relation to operation to selectively emit laser beams of three colors (532 nm (green), 561 nm (yellow), 659 nm (red)).

[A method of Emitting a Laser Beam of 659 nm]

An operator operates the switch 2a to select "red" (659 nm) as the color (wavelength) of a laser beam to be used in a surgical operation. When the red is selected, the HRs 14c and 14e are held out of the optical path of the optical axis L2.

Upon receipt of a trigger signal from the footswitch 3, the control section 20 applies electric current to the LD 12 to thereby excite the rod 11. It is to be noted that both end faces of an Nd:YAG crystal used as the rod 11 are applied with an AR (anti reflective) coating for enhancing transmittance with respect to the light of 1064 nm, 1123 nm, and 1319 nm.

When the rod 11 is excited, the light of 1319 nm is resonated between the HRs 14a and 14b and converted to the second harmonic light thereof, that is, the light of 659 nm, by the NLC 13a disposed on the optical path of the optical axis L2. The thus produced laser beam of 659 nm is allowed to pass through the output mirror 15 and enter the fiber 5. Then, the laser beam delivered into the slit lamp 4 through the fiber 5 is irradiated from an irradiation port of the slit lamp 4 toward the patient's eye.

[A Method of Emitting a Laser Beam of 532 nm]

An operator operates the switch 2a to select "green" (532 nm) as the color (wavelength) of a laser beam to be used in a surgical operation. The control section 20 drives the insertion/removal device 30 to move the HR 14c onto the optical path of the optical axis L2 (in a position indicated by a solid line in FIG. 3). Upon receipt of a trigger signal from the footswitch 3, the control section 20 applies electric current to the LD 12 to thereby excite the rod 11.

When the rod 11 is excited, the light of 1064 nm is resonated between the HRs 14a and 14d and converted to the second harmonic light thereof, that is, the light of 532 nm, by the NLC 13b disposed on the optical path of the optical axis L3. The thus produced laser beam of 532 nm is allowed to pass through the output mirror 15 and enter the fiber 5. Then, the laser beam is irradiated from the irradiation port of the slit lamp 4 toward the patient's eye.

[A Method of Emitting a Laser Beam of 561 nm]

An operator operates the switch 2a to select "yellow" (561 nm) as the color (wavelength) of a laser beam to be used in a surgical operation. The control section 20 drives the insertion/removal device 30 to move the HR 14e onto the optical path of the optical axis L2 (in a position indicated by a dashed line in FIG. 3). The control section 20 then applies electric current to the LD 12 in response to a trigger signal from the footswitch 3, thereby exciting the rod 11.

When the rod 11 is excited, the light of 1123 nm is resonated between the HRs 14a and 14f through the wavelength selecting element 60 and converted to the second harmonic light thereof, that is, the light of 561 nm, by the NLC 13c disposed on the optical path of the optical axis L4. The thus produced laser beam of 561 nm is allowed to pass through the output mirror 15 and enter the fiber 5. Then, the laser beam is irradiated from the irradiation port of the slit lamp 4 toward the patient's eye.

The wave plate 16 is always placed between the rod 11 and the HR 14a when the laser beams of the above three colors (532 nm (green), 561 nm (yellow), 659 nm (red)) are selectively emitted. Thus, the light of three wavelengths (1064 nm, 1123 nm, 1319 nm) emitted from the rod 11 passes through the wave plate 16 and is reflected by the HR 14a, and passes through the wave plate 16 again. As a result, the light whose polarization direction is rotated 90° is returned to the rod 11. This returning of the light having a 90°-rotated polarization direction to the rod 11 can compensate the thermal birefringence effect. Accordingly, the variation in the polarization ratio (P/S) caused by the thermal birefringence effect are reduced, so that such reduced variation has little influence on the wavelength converting efficiency of the NLCs 13a, 13b, and 13c to generate second harmonic light.

FIG. 4 is a table showing the output power of a laser beam of each wavelength (532 nm, 561 nm, 659 nm) and the variation (stability) in the output power in a case that the wave plate 16 is placed on the resonance optical path and in another case without the wave plate 16. The output power of the laser beam of each wavelength increased by as much as ten percent or more. Variations in output power of the laser beam were measured in a limited frequency band of 0 KHz to 1 KHz. From this measurement, it was found that the output power variation was within ±8%. The reason why the frequency band for measurement was limited to the above range is that a laser beam in the frequency band of more than 1 KHz would have output power variations with a smaller amplitude and a lower output energy, so that such laser beam is not worth consideration as a laser beam for surgical operation. As can be seen from this result, the wave plate 16 placed on the resonance optical path allows stable emission of the laser beam of each of the three colors (532 nm, 561 nm, 659 nm).

The above apparatus does not need to be provided with a plurality of wave plates for different wavelengths respectively and to change the wave plates according to the wavelength of light to be emitted. Accordingly, the apparatus of a simple structure can reduce the thermal birefringence effect without needing a complex control and structure.

The present invention may be embodied in other specific forms without departing from the spirit or essential characteristics thereof. For instance, the apparatus in the above embodiment is arranged to emit a laser beam of a wavelength selected from among three different wavelengths, but it is not limited thereto. The wavelength of the laser beam to be emitted can be selected from among multiple wavelengths, for example, two wavelengths, four wavelengths, and more.

Further, although the above embodiment exemplifies the ophthalmic photocoagulation laser apparatus, the present invention is not limited thereto and may be applied to any laser apparatus capable of emitting laser beams of a plurality of different wavelengths.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An ophthalmic laser photocoagulation apparatus capable of emitting laser beams of a plurality of different wavelengths, the apparatus including:
   a solid-state laser medium made of an Nd:YAG crystal which emits light of a plurality of different peak wavelengths;
   a resonance optical system which selectively resonates the emitted light of the plurality of different peak wavelengths and converts respective light to second harmonic light to selectively oscillate the laser beams of the plurality of different wavelengths; and
   a ¼ wave plate for a wide band, which is placed in the resonance optical system and constructed of a combination of a quartz plate and a magnesium fluoride plate to have a property of providing a uniform phase difference to the light of the plurality of different peak wavelengths to be converted, the ¼ wave plate being applied with an anti-reflective coating to enhance transmittance to the light of the plurality of the different peak wavelengths to be converted, wherein the resonance optical system includes:

a first resonance optical system which includes a first wavelength converting element, and resonates the emitted light of a first peak wavelength and converts the light of the first peak wavelength to second harmonic light by the first wavelength converting element to oscillate a first laser beam;

a second resonance optical system which includes a second wavelength converting element and uses a part of an optical path in common with the first resonance optical system, and resonates the emitted light of a second peak wavelength and converts the light of the second peak wavelength to second harmonic light by the second wavelength converting element to oscillate a second laser beam;

a third resonance optical system which includes a third wavelength converting element and uses a part of an optical path in common with the first resonance optical system, and resonates the emitted light of a third peak wavelength and converts the light of the third peak wavelength to second harmonic light by the third wavelength converting element to oscillate a third laser beam;

a first reflection mirror and a second reflection mirror which are placed to be insertable in and removable from different positions of the common use optical path; and an insertion and removal unit which includes a shaft on which the first and second reflection mirrors are attached at different axial angles, the insertion and removal unit being adapted to selectively insert and remove (one or both of) the first and second reflection mirrors such that at most one of the first and second mirrors is in the common use optical path at any time, by rotating the shaft without changing an angle of a reflection plane of each mirror with respect to an optical axis of the common use optical path, wherein the first, second and third resonance optical systems are selectively used in association with insertion/removal of the first and second reflection mirrors, and the ¼ wave plate is placed on the common use optical path.

2. The ophthalmic laser photocoagulation apparatus according to 1, wherein the first, second, and third peak wavelengths are about 1064 nm, about 1123 nm, and about 1319 nm, respectively.

* * * * *